United States Patent [19]

Krebs et al.

[11] 4,049,192
[45] Sept. 20, 1977

[54] BLOOD WASHING METHOD USING A SALINE WASH SOLUTION OF VARYING CONCENTRATION FOR USE WITH BLOOD WASHING APPARATUS

[75] Inventors: Daniel Fritz Krebs, Norwalk, Conn.; Hector Miranda, Yorktown Heights, N.Y.

[73] Assignee: Union Carbide Corporation, New York, N.Y.

[21] Appl. No.: 737,606

[22] Filed: Nov. 1, 1976

[51] Int. Cl.² .................................................. B04B 11/02
[52] U.S. Cl. .................................. 233/14 R; 233/19 R
[58] Field of Search .................... 233/1 R, 1 D, 14 R, 233/14 A, 19 R, 19 A, 27; 210/DIG. 23; 23/258.5 R

[56] References Cited

U.S. PATENT DOCUMENTS

| | | | |
|---|---|---|---|
| 3,452,924 | 7/1969 | Schlutz | 233/14 R |
| 3,655,123 | 4/1972 | Judson | 233/21 |
| 3,737,096 | 6/1973 | Jone et al. | 233/14 R |
| 3,982,691 | 9/1976 | Schlutz | 233/14 R |
| 3,987,961 | 10/1976 | Sinn et al. | 233/14 R |

*Primary Examiner*—George H. Krizmanich
*Attorney, Agent, or Firm*—Frederick J. McCarthy, Jr.

[57] ABSTRACT

A saline wash solution of decreasing concentration is used in the course of washing of blood.

2 Claims, 10 Drawing Figures

BLOOD WASHING METHOD USING A SALINE WASH SOLUTION OF VARYING CONCENTRATION FOR USE WITH BLOOD WASHING APPARATUS

The present invention relates to blood washing using saline solutions and more particularly to the use of a saline solution of constant flow and linearly varying concentration in the course of blood washing.

Blood washing is a procedure known to the art, for example, as described in U.S. Pat. No. 3,982,691—Centrifuge Separation and washing Device and Method—Charles A. Schlutz, issued Sept. 28, 1976. As described in the above-noted U.S. patent human blood from volunteer donors is washed to remove unwanted constituents such as contaminants, toxicants, viruses, medicants, glycerines, cellular debris and the like, using a device based on centrifugal separation. Such a device includes a rotatable enclosure into which liquids, such as blood and wash liquids, e.g. saline solutions are injected, and from which the washed blood, wash liquids and unwanted constituents are removed. While the device described in the above-noted patent can be used to wash blood continuously, in a particular mode of operation, a predetermined amount of blood, e.g. a package available from a blood banking organization, is washed using pre-determined packaged quantities of wash solution. It has been the previous practice in blood washing, e.g. to remove high concentrations of glycerol, to initially use a relatively high concentration saline solution, e.g. about 2-5% concentration, followed by the use of a substantially lower concentration saline solution, e.g. about 8% concentration. The purpose in using a high concentration saline solution followed by a substantially lower saline concentration wash solution is to achieve rapid removal of relatively large amounts of contaminant, e.g. glycerol, while recovering washed blood of a suitably low saline concentration which is not detrimental to the red blood cells.

The sequential use of high and low saline solutions of substantially different concentrations, however, has the potentially undesirable effect of hemolyzing, i.e. bursting the red cells. It is therefore an object of the present invention to provide a method for using saline wash solutions which avoids the contacting the blood with saline solutions of substantially different concentration in the course of blood washing.

Other objects will be apparent from the following description and claims taken in conjunction with the drawing wherein

Figure 1:
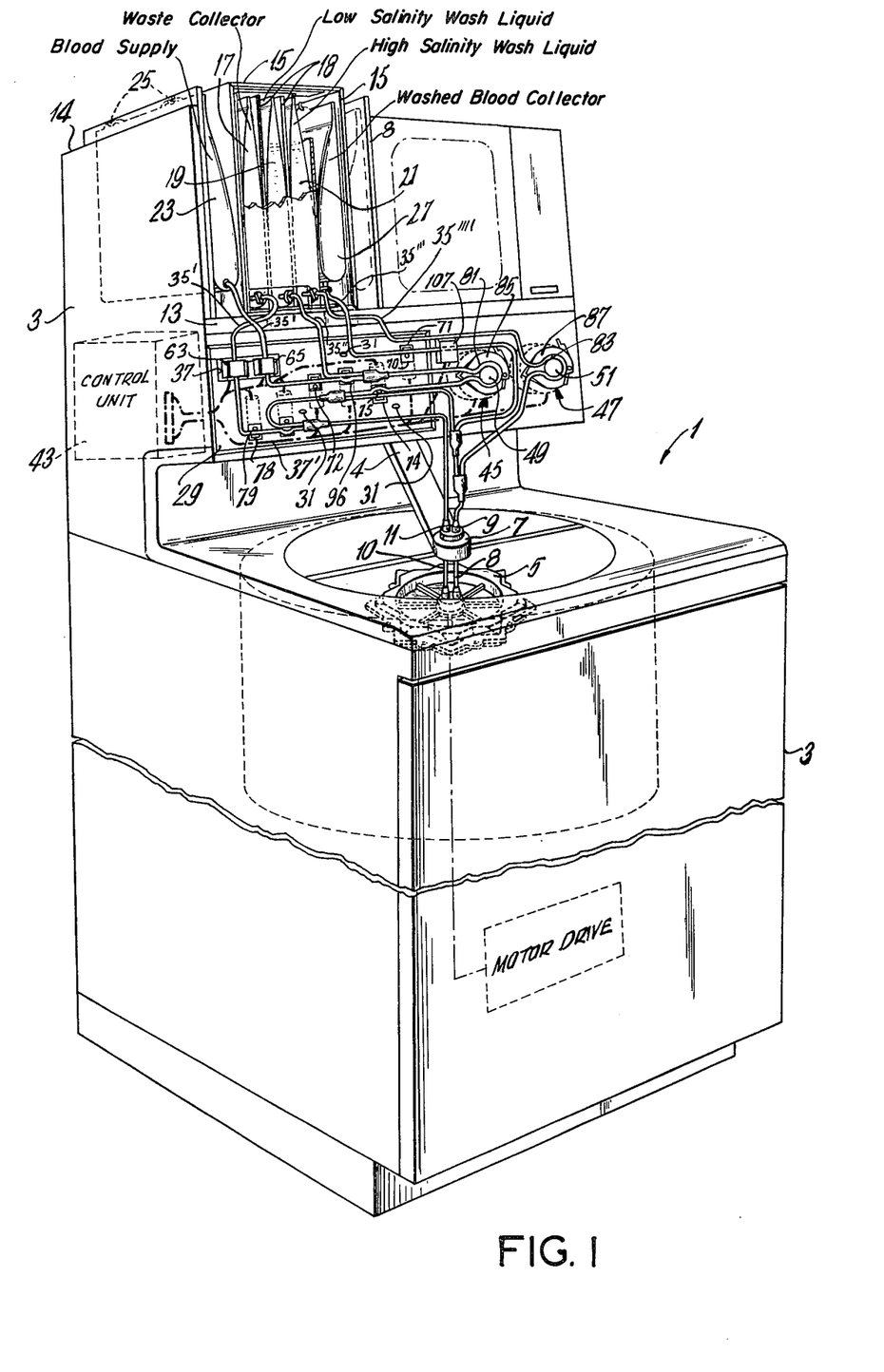
FIG. 1 shows somewhat schematically a blood washing device

With reference to FIG. 1 of the drawing, a blood washing apparatus is indicated at 1 having an enclosing housing 3 in which is contained a rotatable enclosure means 5 such as the type described in the above-noted U.S. Pat. No. 3,982,691 which washes blood cells in the manner described in the patent.

Figures 2, 2A, 2B:
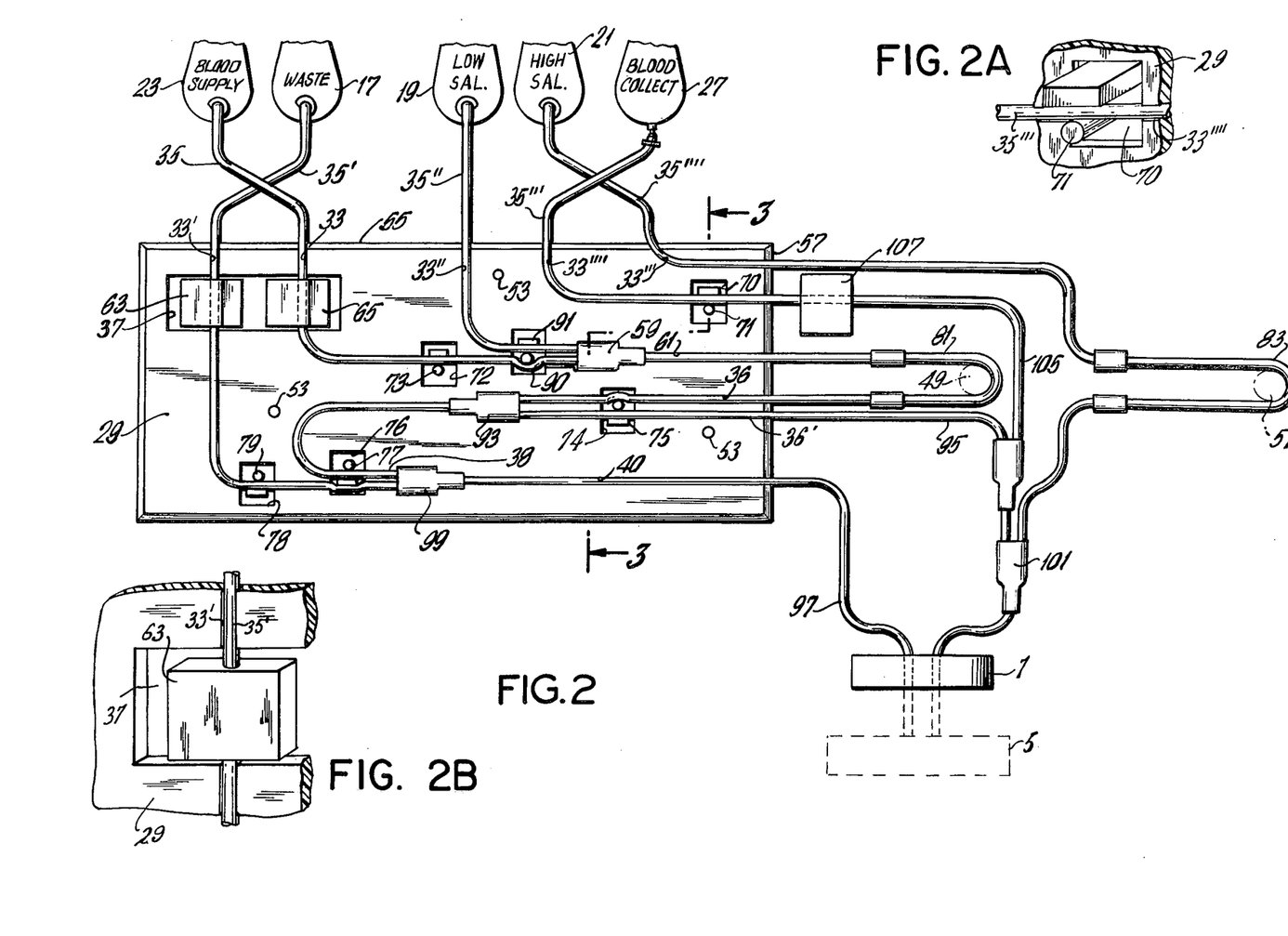
FIGS. 2, 2A, 2B, 3, 4 and 5 show a tubing harness arrangement and details thereof for use with the blood washing device of FIG. 1

The tube harness arrangement 29 shown in FIG. 1 and more particularly in FIG. 2 is disclosed in copending U.S. patent application "Disposable Tubing Harness for Use with Blood Washing Apparatus".

A fluid connector 7, supported on arm 4 above entry conduit 8 and exit conduit 10 provides fluid communication with blood washing enclosure means 5. Fluid connector 7 has two conduits 9 and 11 for the entry and removal of liquid as hereinafter described.

Housing member 3 is provided with a shelf member 13 and side supports 14 and 8 which support a container 15, having partitions 18, e.g. made of cardboard, which supportably holds an initially empty waste package 17, a low concentration saline solution containing package 19, and a high concentration saline solution containing package 21. A blood containing package 23, such as a package obtained from a blood bank, is supported by means of hooks on side support 14 as indicated at 25.

A washed blood collection package 27 initially arranged in container 15, is similarly supported on side support 8 during blood washing. The above-described packages 17, 19, 21, 23 and 27 are suitably made of a transparent flexible plastic material such as polyolefins, polyvinyl chloride and the like.

The horizontally disposed array of adjacent packages 17, 19, 21, 23 and 27 are located above a board-like member 29 which is removably engaged to housing 3 by support pins as indicated at 31. Board-like member 29 is suitably made of polyvinyl chloride, polyurethane and the like and contains grooves 33, 33', etc., as particularly indicated in FIGS. 2 and 4 which respectively engage and securely hold flexible tubes 35, 35', etc., which are transparent and also suitably made of polyvinyl chloride, polyurethane and the like. Board-like member 29 also has openings as hereinafter described to provide clearance for valves 39, 39', etc., and sensors 41, 41', etc., which are mounted on housing 3 and which receive electrical signals from or provide electrical signals to a conventional electrical control unit 43 which is contained within housing 3. Housing 3 also contains conventional peristaltic pumps 45 and 47 which have motor drive shaft extensions 49 and 51 respectively which have cross-sections lying in substantially the same vertical plane as the grooves 33, 33', etc., of board-like member 29. The rotation of the shafts 49 and 51 of pumps 45 and 47 may be controlled by signals from control unit 43.

Figure 3:
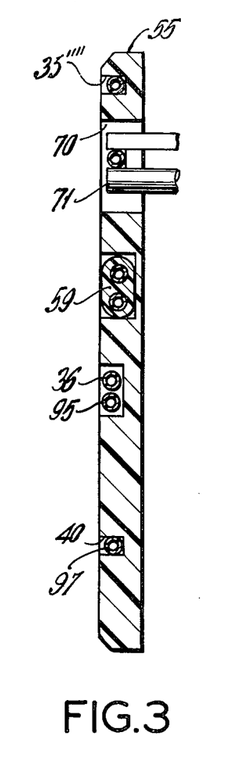
Figure 4:
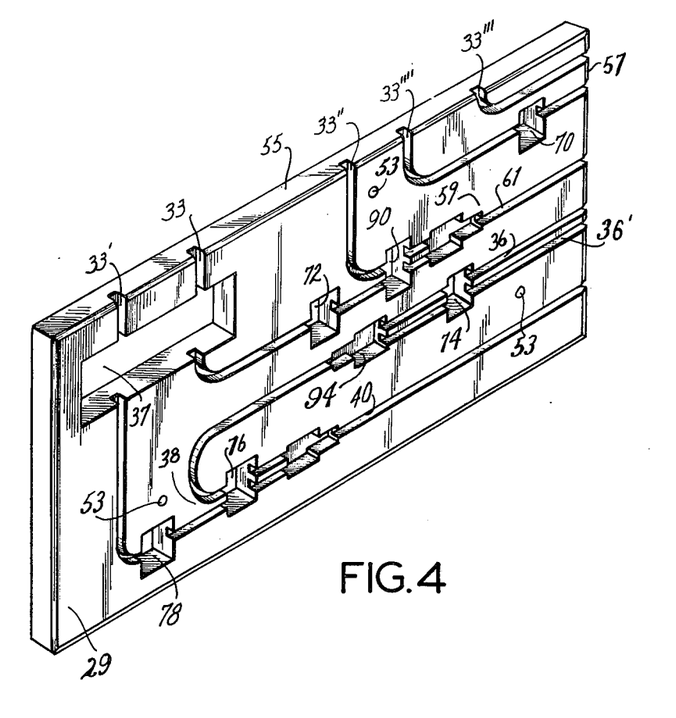
Figure 5:
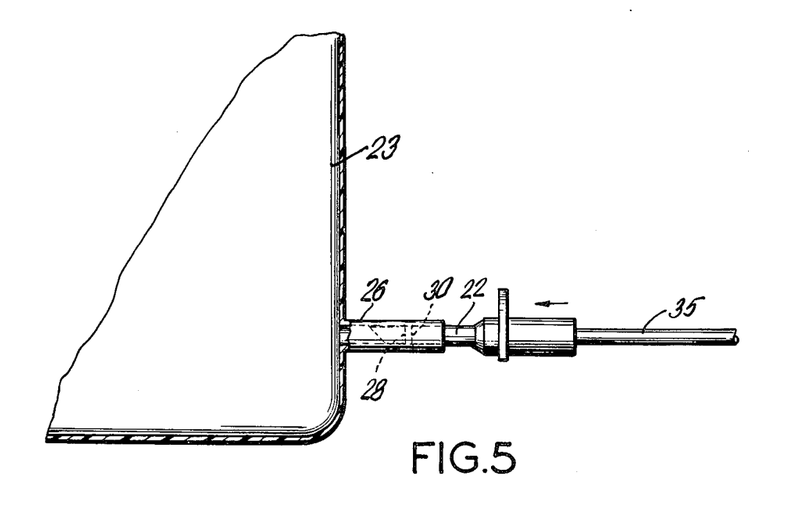

With reference to FIGS. 2, 3 and 4 packages 17, 19, 21, 23 and 27 are connected to flexible tubes 35-35'''', for example by means of a "Spike" connector arrangement as shown in FIG. 5 comprising a pointed extension member 22 which is force fitted by hand in conduit extension 26 and pierces a plastic membrane 30.

Board-like member 29 is mounted on pins arrangement 31 on housing 3 by means of holes 53 in board-like member 29. Each of the flexible conduits 35-35'''' is force fitted into a groove 33-33'''' which extends from the upper edge 55 of board-like member 29 to the side 57 of board-like member 29 which is adjacent the horizontally disposed peristaltic pump shafts 49 and 51 as shown in FIG. 1. An additional groove 36 extends from side 57 into the interior of board-like member 29 to join with groove 33' at 38 into a single groove 40. A further additional groove 39 extends parallel to groove 36 and joins groove 36 at 94. As shown in FIG. 2, grooves 33 and 33'' join at 59 into a single groove 61. Board-like member 29 is provided with openings at locations along various groove paths to accommodate optical sensors 63 and 65, in opening 37, and pinch valves 71, 73, 75, 77, 79 and 91 in openings 70, 72, 74, 76, 78 and 90 respectively. The above-noted optical sensors and pinch valves are mounted on housing 3 and are electrically connected to control unit 43 as shown in FIG. 1.

With the flexible tube 35-35'''' assembled in boardlike 29 and the tubes connected packages 17, 19, 21, 23 and 27 as shown in FIG. 1, loops 81 and 83 are fitted around peristaltic pump shafts 49 and 51 as also shown in FIG. 1 and held fixed with respect to the shafts by clamps 85 and 87 as shown in FIG. 1.

With the tube harness arrangment of the present invention in place as described above, the blood washing apparatus shown in FIG. 1 can be operated. For example, low concentration saline solution from package 19 is pumped by the rotation of peristaltic pump shaft 49 of low salinity pump 45 through tube 35'' to T connection 59, valve 91 being open, to T connection 93 where flow is reversed, due to valve 77 being closed and valve 75 being open, whereby low concentration saline solution passes through tube section 95 via connector 7 into rotating enclosure member 5, thereby priming enclosure member 5. Low saline solution in excess of that required for priming exits enclosure member 5 via connector 7 and tube section 97 through T connection 99 and tube 35' to waste package 17. After priming with low concentration saline solution valve 73 is opened and, blood from package 23 is pumped via tube 35 into enclosure member 5 by the same path as the previously described low concentration saline solution prime. Optical sensor 65 detects the start and finish of blood flow through transparent tube 35 and at the finish provides an electrical signal to control unit 43, shown in FIG. 1, so that signals can be provided to the valves and pumps in the following "wash" step.

In the wash step, pump shaft 49 of low salinity pump 45 and pump shaft 51 of high salinity pump 47 can be both operated to provide a continuous flow of saline solution of predetermined relatively high concentration into enclosure member 5, the higher saline concentration solution proceeding directly from package 21 via flexible tube 35'''' through T connection 101 and connector 7 to enclosure member 5; the low concentration saline solution proceeds from package 19 in the same manner as the above described priming step. During the washing step, saline solution containing contaminants, etc., i.e. waste liquid, is continuously removed from enclosure member to waste package 17 in the same manner as excess saline solution was removed in the above described priming step. When the predetermined washing period is over, the washed blood is collected from enclosure member 5 into package 27 by centrifugal force and the action of pump shaft 49 of low salinity pump 45 which pumps low concentration saline solution from package 19 into enclosure member 5 by way of tube 35'', open valve 91 T connection 59, tubes 81 and 36, T connection 93, open valve 77, T connection 99 and tube 97. The washed blood exits through T connection 101 tube 105, open valve 71 and tube 35''' to blood collection package 27. During the foregoing collection step valves 70 and 75 are closed and pump 50 is deactuated. The passage of washed blood is detected by optical sensor 107 and when blood is no longer detected the pump shaft 49 is stopped by a signal from control unit 43. Optical sensor 63 monitors the flow of waste liquid into waste collector package 17.

The present invention is an improvement in the method of washing blood which method involves the providing of unwashed blood in a rotatable enclosure and thereafter the introduction of saline wash solution into the rotatable enclosure member to contact the blood for a pre-determined period of time to thereby remove contaminants from the blood. The improvement of the present invention comprises decreasing the concentration of saline solution from an initial relatively high concentration to a predetermined lower level at a substantially linear rate while maintaining the flow rate of the saline wash solution at a substantially constant value.

In the present invention, in a "gradient" wash step as above described the speed of pump shafts 49 and 51 of low and high salinity peristaltic pumps 45 and 47 are controlled so that, during a predetermined wash period, a continuous flow of saline solution is introduced, at a constant rate, into rotatable enclosure member 5, the concentration of the saline solution decreasing, at a substantially linear gradient, fromm a relatively high initial concentration at the beginning of the wash step period to a relatively low concentration at the end of the wash step period. The above-described varying saline concentration wash step can follow a previous high saline concentration wash step, the starting saline concentration in the varying concentration, or gradient wash being substantially the same as the saline concentration in the blood after the previous wash step.

Figure 6:
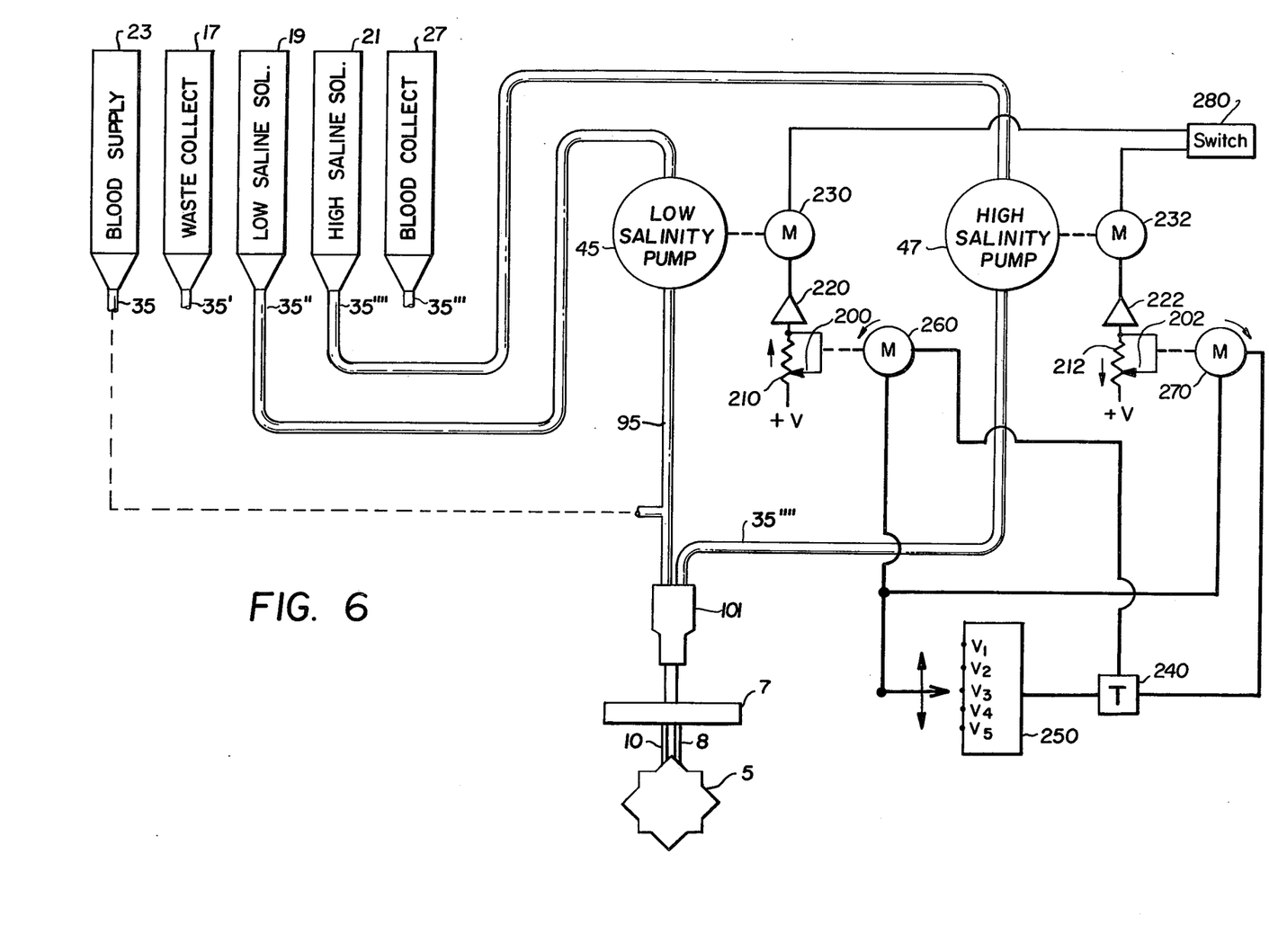
FIG. 6 shows an arrangement for the practice of the method of the present invention in relation to the device of FIG. 1

This will be more clearly understood with reference to FIG. 6. With reference to FIG. 6, the packages 17, 19, 21, 23 and 27 previously shown in FIG. 1 are schematically indicated, together with low salinity pump 45, high salinity pump 47, rotatable enclosure member 5, connector 7, T connector 101, and conduits 35'' and 35'''' for the transfer of saline wash solution to rotatable enclosure member 5. With rotatable enclosure 5 containing blood having a known salinity, e.g. due to a previous saline solution wash, it is desired to lower the salinity of the blood to a predetermined lower salinity concentration. In such a case, the speed of pumps 45 and 41 are initially operated at speeds to provide a flow of saline solution which is substantially the same concentration as that of the blood in rotatable enclosure member 5, and the speeds of pumps 45 and 47 are thereafter adjusted so that over a predetermined period of time, the concentration of the saline solution entering rotatable enclosure member 5 decreases substantially linearly to a predetermined lower value while the flow rate of saline solution into rotatable enclosure member 5 remains constant. The following equations can be used in determining the starting and final pump speeds for such a situation.

$$V_1 = \frac{T}{K_P} \times \frac{S_2 - S_D}{S_2 - S_1}$$

$$V_2 = \frac{T}{K_P} \times \frac{S_D - S_1}{S_2 - S_1}$$

where $V_1$ 32 speed in rpm of low salinity pump 45
$V_2$ = speed in rpm of high salinity pump 47
$T$ = flow rate, e.g. ml per second
$S_1$ = concentration in % of low salinity wash solution
$S_2$ = concentration in % in high salinity wash solution
$S_D$ = concentration in % of desired salinity in wash solution entering rotatable enclosure 5, either start or final $K_p$ = constant for a given pump in ml/revolution of pumps 45 and 47

By way of example, and with reference to FIG. 6, if it is desired that a saline solution enter rotatable enclosure member 5 at a starting concentration of 3% and a final concentration of 2% at a rate of 500 ml per minute for a one minute wash period, the computation using the foregoing formulas is as follows: Assume:

1. concentration of low saline solution in package 19 is 0.8%
2. concentration of high saline solution in package 21 is 5%
3. Kp (pump constant for each pump 81, 83 is 1.25 ml/rev Starting Velocity of Low Salinity Pump 45
$$= \frac{500 \text{ ml/min}}{1.25 \frac{\text{ml}}{\text{rev}}} \times \frac{5\% - 3\%}{5\% - 0.8\%}$$
$$= 190 \text{ rpm}$$

Final Velocity of Low Salinity Pump 45 (after one minute)
$$= \frac{500 \text{ ml/min}}{1.25 \frac{\text{ml}}{\text{rev}}} \times \frac{5\% - 2\%}{5\% - 0.8\%}$$
$$= 286 \text{ rpm}$$

Starting Velocity of High Salinity Pump 47
$$= \frac{500 \text{ ml/min}}{1.25 \frac{\text{ml}}{\text{rev}}} \times \frac{3\% - 0.8\%}{5\% - 0.8\%}$$
$$= \text{rpm } 400 \times \frac{2.2}{4.2}$$

Final Velocity of High Salinity Pump 47 (after one minute)
$$= \frac{500 \text{ ml/min}}{1.25 \frac{\text{ml}}{\text{rev}}} \times \frac{2\% - 0.8\%}{5\% - 0.8\%}$$
$$= 114 \text{ rpm}$$

With the thus calculated starting and final speeds for low salinity pump 45 and high salinity pump 47 and with reference to FIG. 6, the position of arm 200 of variable resistor 210 can be manually positioned to establish the voltage input required for amplifier 220 which provides a voltage to pump motor 230 to cause an initial rotation of 190 rpm for low salinity pump 45. Similarly, arm 202 of variable resistor 212 is positioned so that the voltage to amplifier 222 and drive motor 232 for high salinity pump 47 causes an initial rotation of 210 rpm for high salinity pump 47. The above-described voltages are applied upon actuation of timing switch 240. Under these conditions a saline solution of 3% concentration will enter rotatable enclosure 5. A control unit 250 provides various voltage levels $V_1$, $V_2$, $V_3$, etc., which can be selected and applied to motors 260 and 270 which are mechanically engaged to arms 200 and 202 of variables resistors 210 and 212. Motor 260, when actuated by a selected voltage $V_1$, $V_2$, etc., will rotate at a constant speed and cause arm 200 to move in the direction indicated and the voltage applied to amplifier 220, and hence the speed of low salinity pump drive motor 230 will increase linearly for the period determined by timing switch 240, e.g. one minute, to achieve a higher final value which establishes the final velocity of 286 rpm for low salinity pump 45. The selected voltage $V_1$, $V_2$, etc., required to drive arm 200 of variable resistor 210 can be routinely determined from rpm per volt data for motor 260 and the total voltage applied to resistor 210. Similarly and concurrently motor 270, which is arranged to rotate in the opposite direction to motor 260, when actuated by the selected voltage $V_1$, $V_2$, etc., will cause the voltage applied to amplifier 222, and hence high salinity pump drive motor 232 to decrease linearly for the period determined by timing switch 240, e.g. 1 minute, to achieve a lower final velocity of 114 rpm for high salinity pump 45. Under the above described circumstances, the flow rate of saline solution to rotatable enclosure member 5 remains constant for the gradient wash period, e.g. 1 minute during which time the concentration of the mixed saline solution entering rotatable enclosure member 5 from low salinity package 19 and high salinity package 21, decreases linearly from its initial value, e.g. 3% to a final value, e.g. 2%. This lower concentration of saline solution may be thereafter continued until interruption of line switch 280 which can be manually or automatically operable.

Figure 7:
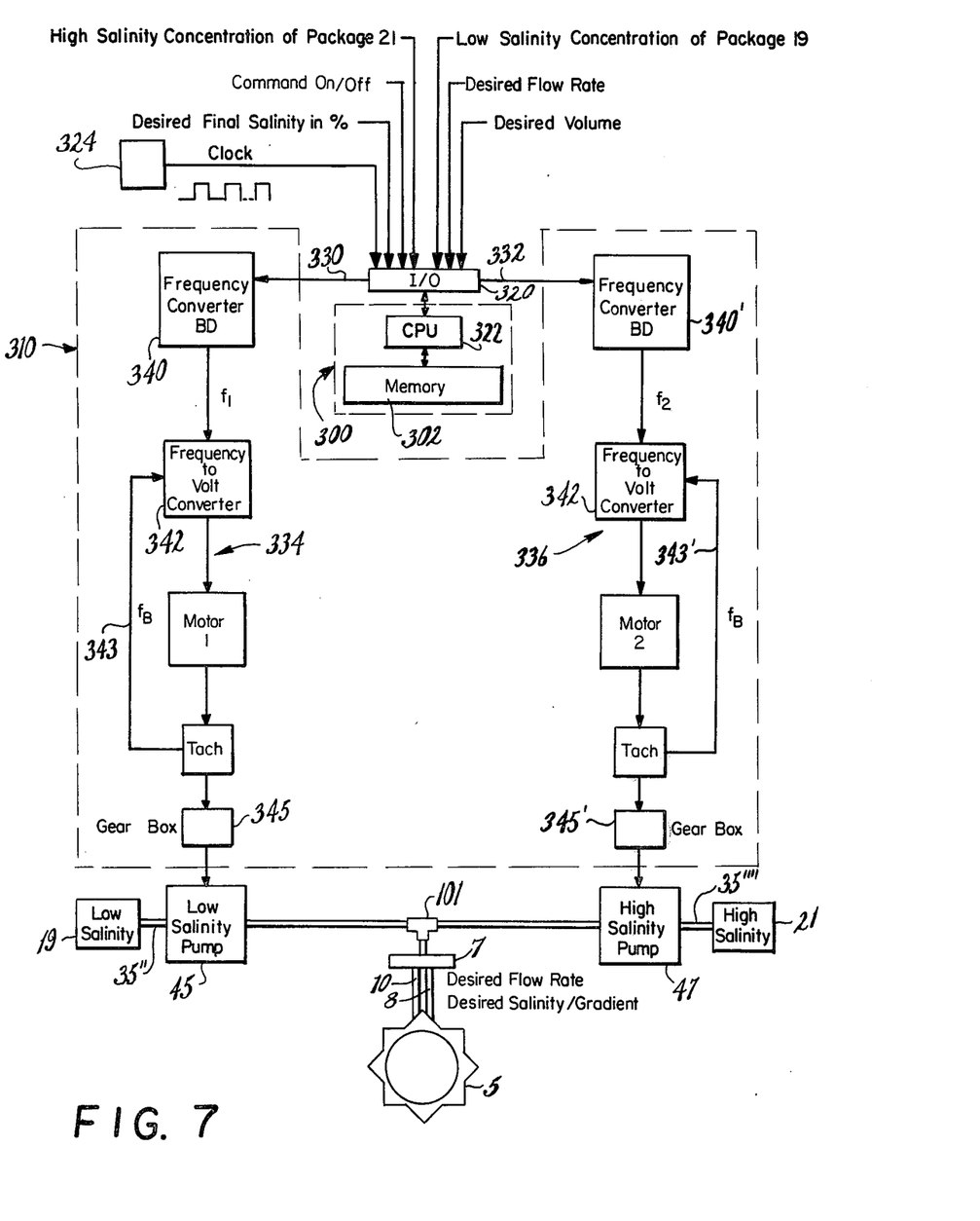
FIGS. 7 and 7a show a further arrangement for the practice of the present invention in relation to the device of FIG. 1.

In a further embodiment of the present invention shown in FIG. 7, low salinity pump 45 and high salinity pump 47 are controlled by a general purpose computer indicated at 300 in combination with a motor control arrangement indicated at 310.

With reference to FIG. 7, values for the concentration of high salinity solution in package 21, e.g. 5% and the value for the concentration of low salinity solution in package 19, e.g. 0.8% are set into the memory 302 of general purpose computer 300 by way of a conventional input-output arrangement 320, e.g. comprising commercially available decimal decoders and flip-flops such as Texas Instrument monolithic devices SN74273, SN7432, SN74LS174, SN7475 and the like. The values for the desired final salinity concentration entering rotatable enclosure 5, e.g. 2%, is set into RAM 430 of processing unit 322 of computer 300 via input-output arrangement 320 as is the desired flow rate, e.g. 500 ml per minute and the desired volume, e.g. 500 ml. The above values are used by the algorithm stored in memory 302 upon actuation of "Command On/Off" signal. Clock 324 provides a series of pulses at a particular time interval for the time period required for the flow of desired volume of saline solution into rotatable enclosure member 5 as hereinafter described. The computer 300 is programmed following the procedure as hereinafter described such that signals are provided by the computer at terminals 330 and 332, at intervals determined by clock 324 which are applied to motor speed control arrangements 334 and 336 respectively to incrementally change the speed of salinity solution pumps 45 and 47. Each speed control arrangement 334, 336 comprises a frequency converter 340, 340' which receives a binary coded command from computer 300 and converts such command to a frequency corresponding to a computed speed for the associated salinity solution pump 45 or 47, which in turn is converted to a voltage at 342, 342' which voltage drives conventional motor-tachometer arrangement 343, 343' at a speed which, after suitable reduction at 345, 345' drives salinity solution pumps 45, 47 at the speed determined by the signals from computer 300.

The memory 302 of computer 300 is conventionally programmed with the equations previously set forth hereinabove, i.e.

$$V_1 = \frac{T}{K_P} \times \frac{S_2 - S_D}{S_2 - S_1}$$

$$V_2 = \frac{T}{K_P} \times \frac{S_D - S_1}{S_2 - S_1}$$

where
- $V_1$ = speed in rpm of low salinity pump 45
- $V_2$ = speed in rpm of high salinity pump 47
- $T$ = flow rate, e.g. ml per second
- $S_1$ = concentration in % of low salinity wash solution
- $S_2$ = concentration in % of high salinity wash solution
- $S_D$ = concentration in % of desired salinity in wash solution entering rotatable enclosure 5, either start or final
- $K_P$ = constant for a given pump in ml/revolution of pumps 45 and 47

The memory 302 of computer 300 is also programmed using an algorithm such as the following:

* Gradient Algorithm

I. Determine the total run time for salinity pumps 45 and 47 by dividing the Desired Volume by the Desired Flow Rate. The total run time in minutes is converted to whole number intervals of clock 324 by multiplying this result by 60/0.2083 = 288 (Total number of clock pulses 324.)

II. Using the above equations determine the change in salinity pump 45 speed by computing the pump speed for the final wash salinity and subtracting from this value the speed of low salinity pump 45 at the start of the wash cycle. This difference, e.g. 96 will yield the number of increments in pump speed for the wash cycle.

III. Compute the number of clock pulses per step interval of pump speed change by dividing runtime, e.g. 288 by the change in low salinity pump 95 speed from start to finish, e.g. 96; 288/96 = 3 pulses of clock 324.

IV. Increment the speed of low salinity pump 45 and decrement the speed of high salinity pump 47 by 1 rpm at the end of each step interval, e.g. 0.625 seconds, for 96 intervals. (3 × 0. 2083)

*arbitrarily selected factor of convenience.

The following is a sample computation using the foregoing algorithm and the same numerical values as the previous example hereinabove.

EXAMPLE

Gradient wash from 3.0% to 2% at a flow rate of 500 ml/min for a total volume of 500 ml.

I. Compute runtime:

$$\frac{\text{Volume}}{\text{flowrate}} = \frac{500 \text{ ml}}{500 \text{ ml/min}} = 1 \text{ min} = 60 \text{ sec.}$$

clock minimum timer interval for clock 324 = 0.2083 seconds number of clock intervals in 1 minute = 60/0.2083 = 288

II. For a 3% wash, the low salinity pump 45 will initially run at 190 rpm and the high salinity pump 47 will run initially at 210 rpm.

III. For a 2% wash, the final low salinity pump 45 speed is 286 rpm and the final speed of high salinity pump 51 is 114 rpm.

IV. The change in speed of low salinity pump 45:
(Pump 45 speed at 3%) − (Pump 45 speed at 2%); 286 − 190 = 96
This represents the number of speed increments for the gradient wash period.

V. Compute step interval:

$$\frac{\text{runtime}}{\text{Pump 45}} = \frac{288}{96} = 3$$

3 × 0.2083 = 0.625 seconds

At the end of each 0.625 seconds the speed of pump 45 is increased and the speed of pump 47 is decreased by 1 rpm. There will be 96 increments during which the change in pump speeds is 1 rpm per interval.

The following chart will show the gradient in salinity generated by the algorithm.

| Time | Speed of Pump 45 (rpm) | Speed of Pump 47 (rpm) | % Salinity |
|---|---|---|---|
| to | 190 | 210 | 3% |
| to + 0.625sec | 191 | 209 | 2.99%* |
| to + 96 × 0.625sec | 286 | 114 | 2% |

*by computation using $S = \dfrac{R_1 S_1 + R_2 S_2}{R_1 + R_2}$

The sum of Pump 45 Speed + Pump 47 Speed is constant, therefore the flow rate of 500 ml/min is constant throughout the gradient wash period.

Figure 7A:
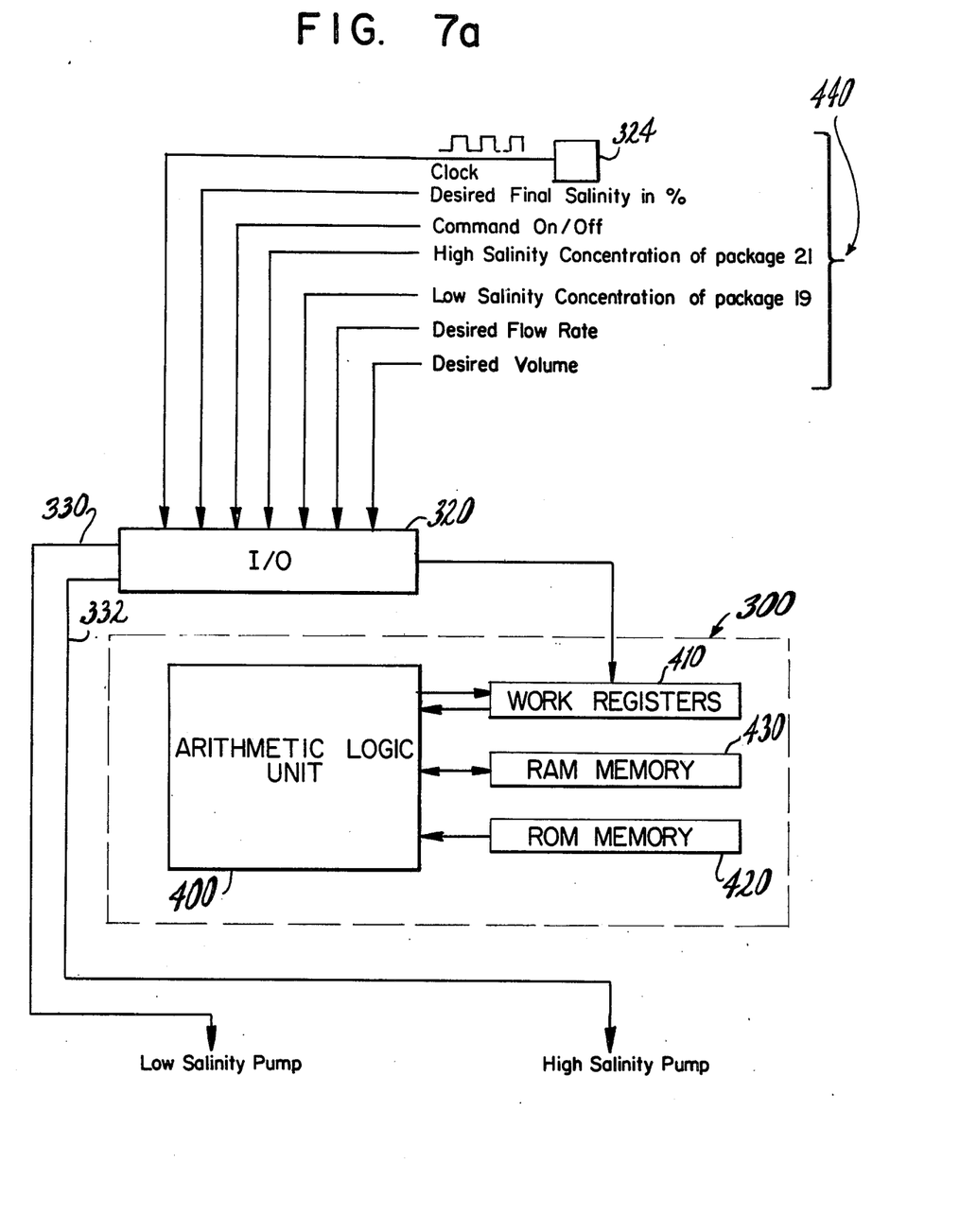

With reference to FIG. 7a, the computer 300 of FIG. 7 is more particularly described by having an arithmetic logic unit (ALU) 400 in combination with work registers 410 to constitute a central processing unit (CPU) which can be an Intel Corporation Silicon Gate microprocessor MOS 8080A. A read only memory unit ROM420, which can be an Intel Corporation Silicon Gate MOS Reprogrammable Read Only memory model 1702A, is routinely programmed with the equations noted above in the algorithm. A random access memory RAM430, e.g. an Intel Corporation Silicon Gate MOS random access memory model 2102A, is also provided to provide temporary storage of values calculated in ALU400, The input values indicated at 440 are used by the algorithm stored on actuation of the "Command On/Off". The set value of High Salinity Concentration of Package 21 and Low Salinity Concentration of Package 19 are transferred to RAM memory 430 for use by the algorithm stored in ROM 420. ROM 420 instructs ALU 400 according to the program in ROM 420. ALU 400 together with Work Registers 410 and RAM memory 430 compute the signals which are provided at intervals at 330 and 332 to control the speed of low salinity pump 45 and high salinity pump 47 as hereinabove described.

What is claimed is:

1. In a method of washing blood by providing blood in a rotatable enclosure member and thereafter introducing saline wash solution into said rotatable enclosure member to contact said blood for a pre-determined washing period and thereby remove contaminants therefrom the improvement which comprises decreasing the concentration of the introduced saline solution from an initial relatively high concentration to a predetermined lower concentration at a substantially linear rate while maintaining the flow rate of the saline solution at a constant value throughout the washing period.

2. Method in accordance with claim 1 wherein a flow of relatively high concentration saline soluton and a flow of relatively low concentration of saline solution are mixed, the flow rate of the low concentration saline solution being increased at a constant rate while the flow rate of the high concentration saline solution decreases at a constant rate, the sum of the flow rate of the high concentration saline solution and the flow rate of the low concentration saline solution being a constant value.

* * * * *